United States Patent [19]

Wayland

[11] Patent Number: 4,806,004

[45] Date of Patent: Feb. 21, 1989

[54] SCANNING MICROSCOPY

[75] Inventor: J. Harold Wayland, Pasadena, Calif.

[73] Assignee: California Institute of Technology, Pasadena, Calif.

[21] Appl. No.: 72,150

[22] Filed: Jul. 10, 1987

[51] Int. Cl.⁴ .............................................. G02B 21/06
[52] U.S. Cl. ................................. 350/527; 350/507; 350/523
[58] Field of Search .................. 350/6.8, 6.91, 6.3, 350/235, 448, 507, 510, 516, 517, 523, 524, 527

[56] References Cited

U.S. PATENT DOCUMENTS

| | | | |
|---|---|---|---|
| 1,116,949 | 11/1914 | Stille . | |
| 3,517,980 | 12/1970 | Petran et al. | 350/527 |
| 3,544,190 | 12/1970 | Moorhosen et al. | 350/6.3 |
| 3,547,512 | 12/1970 | Baer | 350/6.91 |
| 3,926,500 | 12/1975 | Frosch et al. | 350/527 |
| 4,003,636 | 1/1977 | Goshima et al. | 350/448 |
| 4,011,748 | 3/1977 | Bond et al. | 350/523 |
| 4,170,398 | 10/1979 | Koester | 350/6.8 |
| 4,323,299 | 4/1982 | Roberts | 350/523 |
| 4,383,733 | 5/1983 | Weiss et al. | 350/6.3 |

FOREIGN PATENT DOCUMENTS 128936 2/1968 Czechoslovakia .
128937 2/1968 Czechoslovakia .

OTHER PUBLICATIONS

*A Flying-Spot Microscope*, J. Z. Young and F. Roberts, Feb. 10, 1951, issue of Nature, p. 231.

M. Petran, M. Hadravsky, M. D. Egger and R. Galambos, *Tandem-Scanning Reflected-Light Microscope*, Journal of the Optical Society of America, vol. 58, May 1968, pp. 661–664.

W. T. Welford, *On the Relationship Between the Modes of Image Formation in Scanning Microscopy and Conventional Microscopy*, Journal of Microscopy, vol. 96, Aug. 1972, pp. 105–107.

C. J. R. Sheppard and A. Choudhury, *Image Formation in the Scanning Microscope*, Optica Acta, 1977, vol. 24, pp. 1051–1073.

C. J. R. Sheppard and T. Wilson, *Image Formation in Scanning Microscope with Partially Coherent Source and Detector*, Optica Acta, 1978, vol. 25, pp. 315–325.

G. J. Brakenhoff, P. Blom and P. Barends, *Confocal Scanning Light Microscopy with High Aperture Immersion Lenses*, Journal of Microscopy, vol. 117, Nov. 1979, pp. 219–232.

G. J. Brakenhoff, *Imaging Modes in Confocal Scanning Light Microscopy (CSLM)*, Journal of Microscopy, vol. 117, Nov. 1979, pp. 233–242.

M. Petran, M. Hadravsky, J. Benes, R. Kucera and A. Boyde, *Part 1—the Principle, and Its Design*, and *Part 2—Pre-Micro '84 Applications at UCL*, Proceedings RMS, vol. 20, May 1985, pp. 125–139.

H. Wayland, *Laser Stimulation of Fluorochromes in Intravital Microscopy Using a Mirror Objective*, published in Methodology in Microcirculation, pp. 19–24, 7th European Conf. on Microcirculation, Aberdeen, 1972.

H. Wayland and W. G. Freasher, Jr., *Intravital Microscopy on the Basis and Application of an Intravital Microscope for Microvascular and Neurophysiological Studies*, pblsh. Modern Tech. in Physiological Sciences, Academic Press, London 1978, pp. 125–153.

H. Wayland, *Intravital Microscopy*, published in Advances in Optical and Electron Microscopy, Academic Press, vol. 6, 1979, pp. 1–47.

Primary Examiner—John K. Corbin
Assistant Examiner—Martin Lerner
Attorney, Agent, or Firm—Benoit Law Corporation

[57] ABSTRACT

Methods and apparatus for improving contrast and resolution of a predetermined response of an object to illumination, render a two-dimensional array of light spots translatorily movable in a plane of the array, and scan the object by translatorily moving the two-dimensional array of light spots over the object. Sequential signals of light from the object scanned with that translatorily moving two-dimensional array of light spots may be viewed, or sequential reponses of the object to that translatorily moving two-dimensional array of light spots may be recorded or stored for subsequent reproduction and observation.

35 Claims, 4 Drawing Sheets

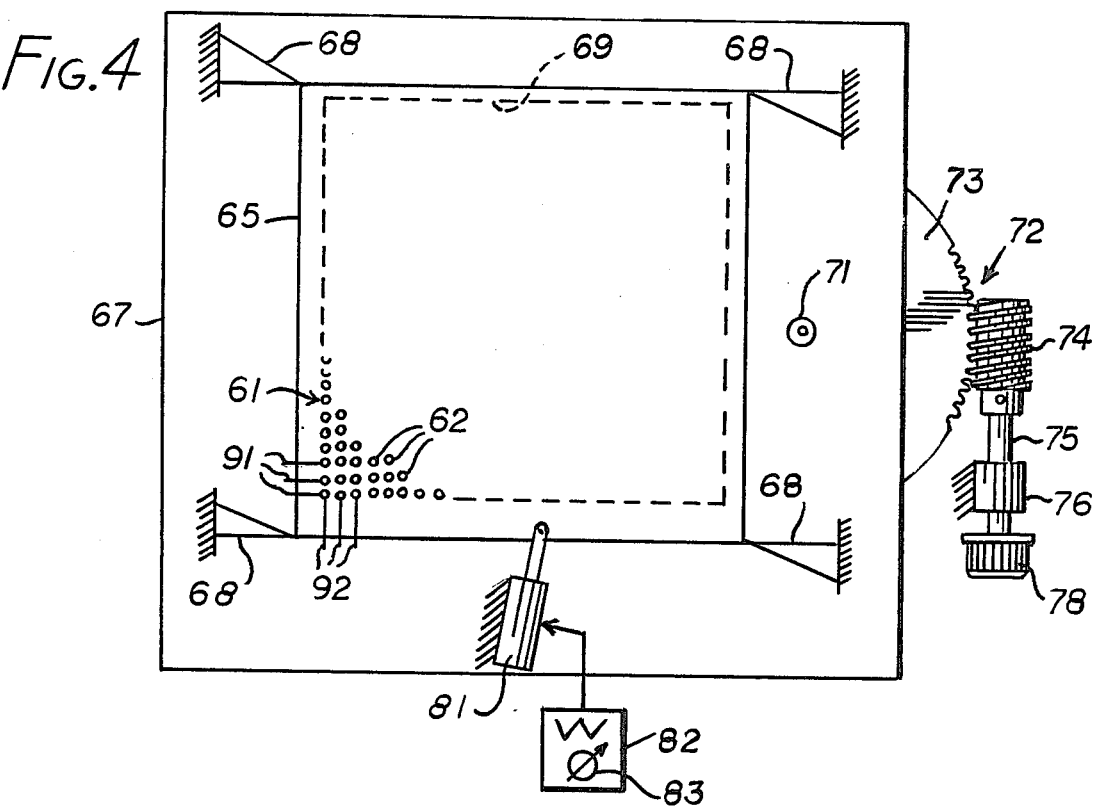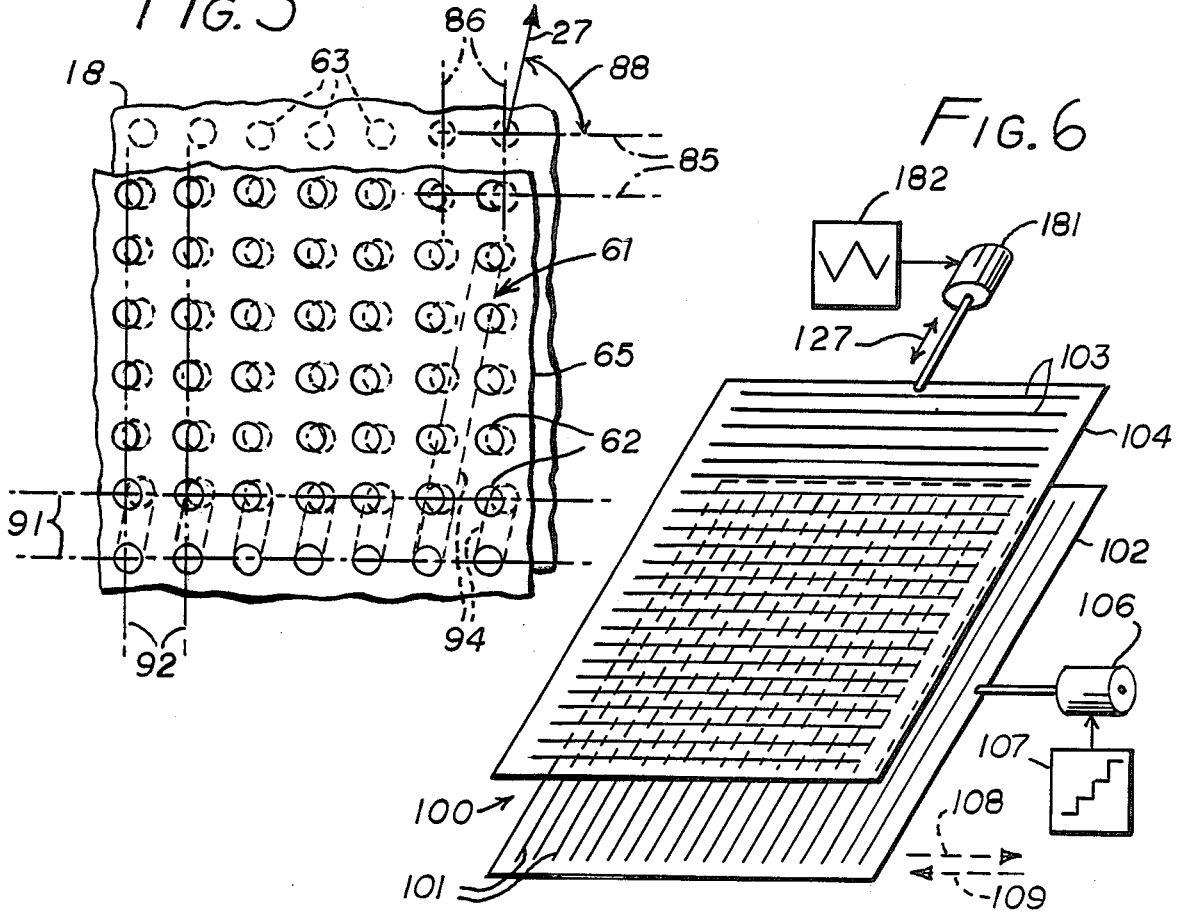

SCANNING MICROSCOPY

BACKGROUND OF THE INVENTION

1. Field of the Invention

The subject invention relates to methods and apparatus for improving contrast and resolution of a predetermined response of an object to illumination, to methods and apparatus having such improved contrast and resolution, and, more specifically, to microscopy and similar techniques in which an object is scanned by an array of light spots.

2. Information Disclosure Statement

The following disclosure statement is made pursuant to the duty of disclosure imposed by law and formulated in 37 CFR 1.56(a). No representation is hereby made that information thus disclosed in fact constitutes prior art, inasmuch as 37 CFR 1.56(a) relies on a materiality concept which depends on uncertain and inevitably subjective elements of substantial likelihood and reasonableness and inasmuch as a growing attitude appears to require citation of material which might lead to a discovery of pertinent material though not necessarily being of itself pertinent. Also, the following comments contain conclusions and observations which have only been drawn or become apparent after conception of the subject invention or which contrast the subject invention or its merits against the background of developments which may be subsequent in time or priority.

Also, no preamble of any statement of invention or claim hereof is intended to represent that the content of that preamble is prior art, particularly where one or more recitations in a preamble serve the purpose or providing antecedents for the remainder of a statement of invention or claim.

In a Letter to the Editors, in the Feb. 10, 1951 issue of NATURE, page 231, J. Z. Young and F. Roberts proposed a flying-spot microscope, suggesting that resolution should be substantially greater with the flying-spot than with a conventional microscope, since only one resolvable region is illuminated at a time. Young and Roberts also considered the possibility of quantitative analysis as perhaps the most important of all advantages of a flying-spot microscope.

Some seventeen years later, M. Petran, M. Hadravsky, M. D. Egger and R. Galambos, published their article entitled *Tandem-Scanning Reflected-Light Microscope*, in the Journal of the Optical Society of America, vol. 58, May 1968, pp. 661 to 664. That article disclosed a principle which was patented in several countries, including the United States, which issued U.S. Pat. No. 3,517,980 to M. Petran and M. Hadravsky on Jun. 30, 1970, for Method and Arrangement for Improving the Resolving Power and Contrast.

The heart of the tandem-scanning reflected-light microscope by Drs. Petran and Hadravsky is a rotating scanning disk in the form of a Nipkow wheel having a multitude of holes arranged in an Archimedean spiral. Predetermined ones of those holes were illuminated for the formation of a continuous stream of light spots scanning the object when the Nipkow wheel was rotated, while conjugate holes on that rotating disk or scanning wheel pass the reflected portion of light to an eye piece or similar device for observation.

There followed theoretical treatments of scanning microscopy, as may be seen from W. T. Welford, *On the relationship between the modes of image formation in scanning microscopy and conventional microscopy*, Journal of Microscopy, Vol. 96, August 1972, pp. 105–107, C. J. R. Sheppard and A. Choudhury, *Image formation in the scanning microscope*, OPTICA ACTA, 1977, Vol. 24, pp. 1051–1073, C. J. R. Sheppard and T. Wilson, *Image formation in scanning microscopes with partially coherent source and detector*, OPTICA ACTA, 1978, Vol. 25, pp. 315–325, G. J. Brakenhoff, P. Blom and P. Barends, *Confocal scanning light microscopy with high aperture immersion lenses*, Journal of Microscopy, Vol. 117, November 1979, pp. 219–232, and G. J. Brakenhoff, *Imaging modes in confocal scanning light microscopy (CSLM)*, Journal of Microscopy, Vol. 117, November 1979, pp. 233–242.

The Tandem Scanning Reflected Light Microscope (TSRLM) appeared again in the literature in the form of two articles by M. Petran, M. Hadravsky, J. Benes, R. Kucera and A. Boyde, comprising *Part 1—the principle, and its design*, and *Part 2—Pre—Micro '84 Applications at UCL*, Proceedings RMS, Vol. 20, May 1985, pp. 125–139, dealing primarily with application of the TSRLM to dental research and related activities.

For further background on intravital microscopy, reference may be had to my article entitled *Intravital Microscopy on the Basis of Telescopic Principles: Design and Application of an Intravital Microscope for Microvascular and Neurophysiological Studies*, published in MODERN TECHNOLOGY IN PHYSIOLOGICAL SCIENCES, Academic Press, London, 1973, pp. 125–153, my article *Laser Stimulation of Fluorochromes in Intravital Microscopy Using a Mirror Objective*, published in METHODOLOGY IN MICROCIRCULATION, pp. 19–24, 7th European Conference on Microcirculation, Aberdeen, 1972, and my article entitled *Intravital Microscopy*, published in ADVANCES IN OPTICAL AND ELECTRON MICROSCOPY, Academic Press, vol. 6, 1979, pp. 1–47.

In addition to the utility mentioned in the further course of this disclosure, the methods and apparatus of the subject invention and of its embodiments herein disclosed also have utility in intravital microscopy, to name a further example.

SUMMARY OF THE INVENTION

It is a general object of this invention to advance scanning microscopy beyond the state of the art manifested by the above mentioned articles.

It is a related object of this invention to extend the utility of scanning microscopy into fields other than proposed so far.

It is a germane object of this invention to avoid the slowness of performance and the effects of delay inherent in single-spot microscopy.

It is also an object of this invention to avoid the high expense and any difficulty in manufacture and operation resulting from the need of rotating scanners or tandem scanning Nipkow disks in microscopy with scanning light spot arrays.

It is a related object of this invention to use the same apertures of a scanning plate or assembly for both light going to the object and light reflected by the object in microscopy.

It is also an object of this invention to provide scanning microscopy and similar systems for both incident light and transillumination work.

Other objects of the invention will become apparent in the further course of this disclosure.

From one aspect thereof, the subject invention resides in a method of improving contrast and resolution of a predetermined response of an object to illumination. The invention according to this aspect resides, more specifically, in the improvement comprising, in combination, the steps of, or means for, making a two-dimensional array of light spots translatorily movable in a plane of the array, and scanning the object by translatorily moving that two-dimensional array of light spots over the object.

From a related aspect thereof, the invention resides in the improvement comprising, in combination, the steps of, or means for, providing a two-dimensional array of light-transmitting apertures, transmitting light through these apertures to provide a two-dimensional array of light spots on the object, and scanning the object with that two-dimensional array of light spots by translatorily moving said two-dimensional array of light-transmitting apertures relative to the object in the plane of that array while transmitting light through the apertures.

In both instances, and in general, sequential signals of light from the scanned object, or sequential responses of the object to the translatorily moving two-dimensional array of light spots, may be viewed, or may be recorded or stored for subsequent reproduction, viewing or data processing.

According to a preferred embodiment of the invention, a travel of translatory movement as required for coverage of the object is varied by adjustment of a sweep angle of that translatory movement.

Other aspects of the invention will become apparent in the further course of this disclosure, and no restriction to any aspects or objects is intended by this Summary of the Invention.

BRIEF DESCRIPTION OF THE DRAWINGS

The subject invention and its various aspects and objects will become more readily apparent from the following detailed description of preferred embodiments thereof, illustrated by way of example in the accompanying drawings, in which like reference numerals designate like or functionally equivalent parts, and in which:

FIG. 4 is a top view of a scanning assembly according to an embodiment of the invention, which may be employed in any of the embodiments shown in FIGS. 1 to 3, for instance;

FIG. 5 is a detail view of part of an aperture plate used in the embodiment of FIG. 4, and shown superimposed on a corresponding portion of an object being scanned and observed; and FIG. 6 is a somewhat exploded perspective view of a scanning light spot producing assembly according to a further embodiment of the subject invention which, for instance, may be employed in any of the embodiments shown in FIGS. 1 to 3 hereof.

DESCRIPTION OF PREFERRED EMBODIMENTS

Figure 1:
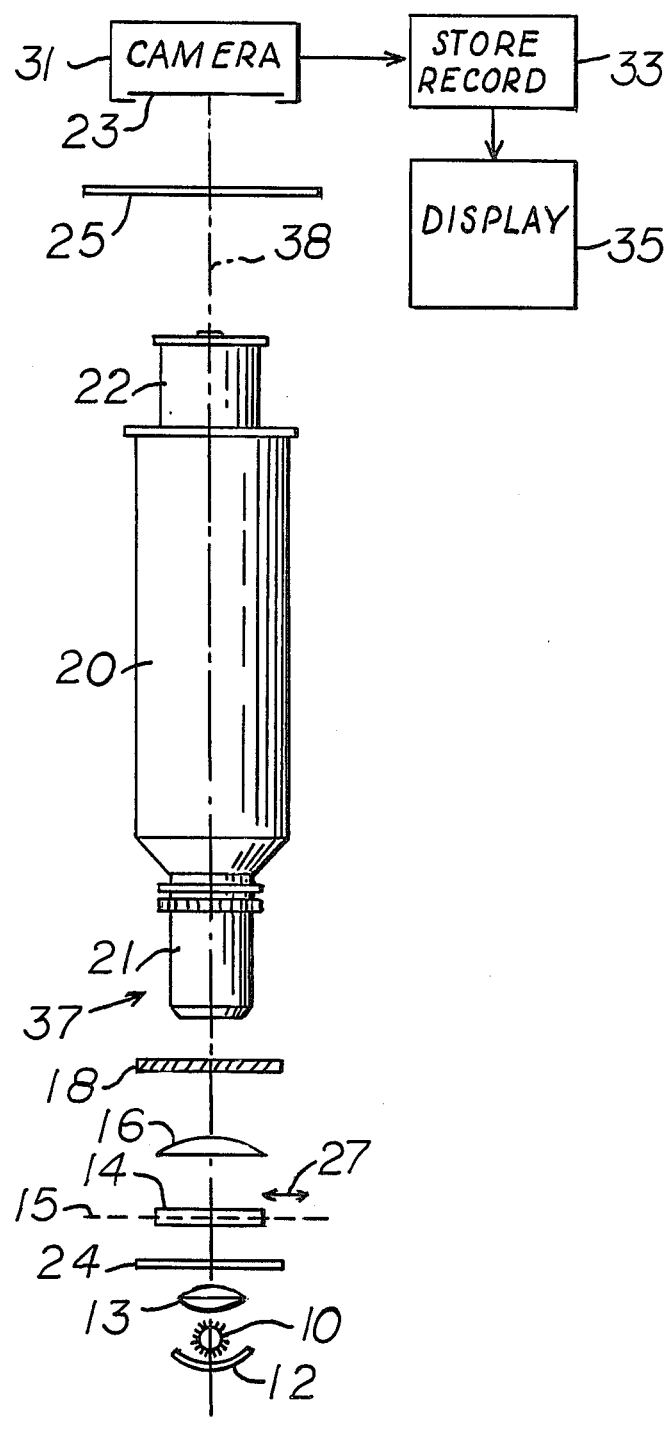
FIG. 1 is a somewhat diagramatic elevation of a transillumination-type scanning microscopy system according to an embodiment of the subject invention.

Embodiments of the invention shown in the drawings may be used for transillumination-type of scanning microscopy or "Type 1 Scanning," or incident-light-type microscopy or "Type 2 Scanning." Ordinary microscope or telescopic systems may be used. Polarized light or fluorescence may be employed.

The symbolically illustrated light source 10 may, for instance, be or include an incandescent or arc lamp or other area light source provided with a conventional concave mirror or reflector 12. By way of further example, the symbolically illustrated light source 10 may be a laser.

The light source 10 is provided with a collecting lens 13 which in effect images the light source onto the image plane of the scanning assembly 14. In other words, the image plane 15 of the collecting lens and the planar scanning assembly 14 coincide. The collecting lens 13 thus puts a real image of the light source 11 into the image plane 15 and thereby into the plane of the translatory scanning assembly 14.

A condenser 16, in turn, images the apertured scanning assembly 14 onto the plane of the object 18 being observed, or into any desired plane within that object.

What may be an ordinary microscope 20 has an objective lens system 21 and a viewing or imaging ocular 22 which forms an optical image 23 for viewing, recording or storage.

Further components in the apparatus of FIG. 1 and of other figures may include a first filter 24 and a second filter 25, having such other components as the translatory scanner 14, condenser 16, objective lens system 21, ocular 22, and even the object 18, therebetween.

The filters 24 and 25 need not necessarily be used in pairs. For instance, the filter 24 may be a heat-absorbing, ultraviolet-eliminating, band-pass or other optical filter customarily used in microscopy.

On the other hand, the first filter 24 may be a filter for conditioning the light from the source 10 for action on the object 18, while the second filter 25 may be a filter for conditioning the light transmitted or reflected by the object 18 for viewing, recording or storage, as the case may be. In practice, this may also include a function of the filter 25 which eliminates undesired light.

For instance, in fluoroscopy, the first filter 24 may be an excitation filter passing light from the source 10 that will excite fluorescence in the object 18. Such fluorescence may be natural or may be induced by fluorescein, rhodamine, indocyanin, or any of the dozens of other substances used to induce fluorescence in an object.

In essence, if 24 is an excitation filter, then such filter will only pass light in a wavelength range that excites the desired fluorescence in the object 18. In practice, the wavelength of the light source 10 may also be selected for that purpose. For instance, an Argon laser may be employed, if that excites the desired fluorescence in the object, and so forth.

The second filter 25 may be a filter that complements the function of the first filter 24. For instance, if the first filter 24 is an excitation filter passing relatively short wavelengths, such as the wavelength at or below the blue region, then the filter 25 may be a barrier filter passing the light of the longer wavelengths resulting from the operation of the fluorescent material in the object 18.

In this respect, the first and second filters 24 and 25 accommodate the fact that fluorescence in the object 18 performs a kind of wavelength transformation, in effect shifting the light output of the object toward longer wavelengths relative to the light input of that object 18.

Alternatives within the scope of the invention include the use of polarizers at 24 and 25. For instance, the input filter 24 may be a polarizer which polarizes light from the source 10, while the output filter 25 may be an analyzer which prevents reflected light and the like from reaching the optical image 23, as more fully described below.

According to the subject invention, the scanning aperture assembly 14 moves only translatorily, as indicated by the double-headed arrow 27, and as more fully disclosed below.

Briefly, the scanning assembly 14 has or provides a two-dimensional array of light-transmitting apertures, as more fully shown below, while the light source 10 collecting lens 13, with or without reflector 12 and filter 24, transmits light through these apertures to provide a two-dimensional array of light spots on the object 18. Within the scope of the subject invention, the latter phrase is intended to be sufficiently broad to cover also instances in which the two-dimensional array of light spots is provided at a desired level in the object.

In either case, the object 18 is scanned with that two-dimensional array of light spots by translatorily moving the two-dimensional array of light-transmitting apertures relative to the object in the plane of that array, as indicated by the double-headed arrow 27, while transmitting light through the apertures in the scanning assembly 14 with the light source 10, collecting lens 13, etc.

As indicated in FIG. 1 at 31, the optical image 23 may be projected into a camera. By way of example, the camera 31 may be a human eye, in which case 23 is a virtual image, as provided by the microscope 20, including an appropriate viewing ocular 22.

On the other hand, the optical image 23 may be projected with a imaging ocular or similar lens system at 22 onto film or another light-sensitive medium in a photographic camera, or onto the target of a video camera at 31.

The microscope 20, with or without filter 25 and camera 32 may thus be used for viewing sequential signals of light from the object 18 scanned with the translatorily moving two-dimensional array of lights spots. As indicated at 33, sequential responses of the object 18 to the translatorily moving two-dimensional array of light spots may be recorded or stored, such as with the aid of a video tape recorder or digital memory connected to the camera 31.

In the case of a video camera, the camera 31 needs to be synchronized with the scanning 27 of the two-dimensional arrays of light spots of the object 18. A video camera with a charge-coupled device (CCD) type target may be used at 31.

Such a CCD type camera 31 typically has a sensing cycle, during which light from the two-dimensional array of light spots in the object 18 is stored in a frame in the camera. That frame is then transferred from one CCD section to another, such as by broadsiding to a readout section, from which electric camera output signals may be transferred to the storage or recording facility 33. In practice, these signals may represent reflections or transmissions of light from the above mentioned two-dimensional array of light spots, or the result of fluorescence induced by such light spots translatorily scanning the object 18, as the case may be.

In practice, frame transfer within the camera 31 may not be necessary, if time lapse between readout and resumption of sensing is permitted.

The stored electric signals may be subjected to data processing, depending on the objective of any particular observation. A video monitor or other display apparatus 35 may be connected to the storage or recording facility 33 for observation of the results of the luminous scanning of the object 18, if desired on a continuous basis.

In FIG. 1, the components of the microscopic apparatus 37, from light source 10 or reflector 12, to camera 31 or camera target at 23, are arranged on a straight axis 38. However, this need not necessarily be the case. For instance, mirrors could be employed in the light path in order to deflect incident, transmitted or reflected light. In this respect, one or more beam splitters or dichroic mirrors may be employed in the apparatus. For instance, in the case of fluoroscopy, a dichroic mirror may be provided at 25 for separating undesired short-wavelength emanations from the longer wavelength emissions to be observed.

Figure 2:
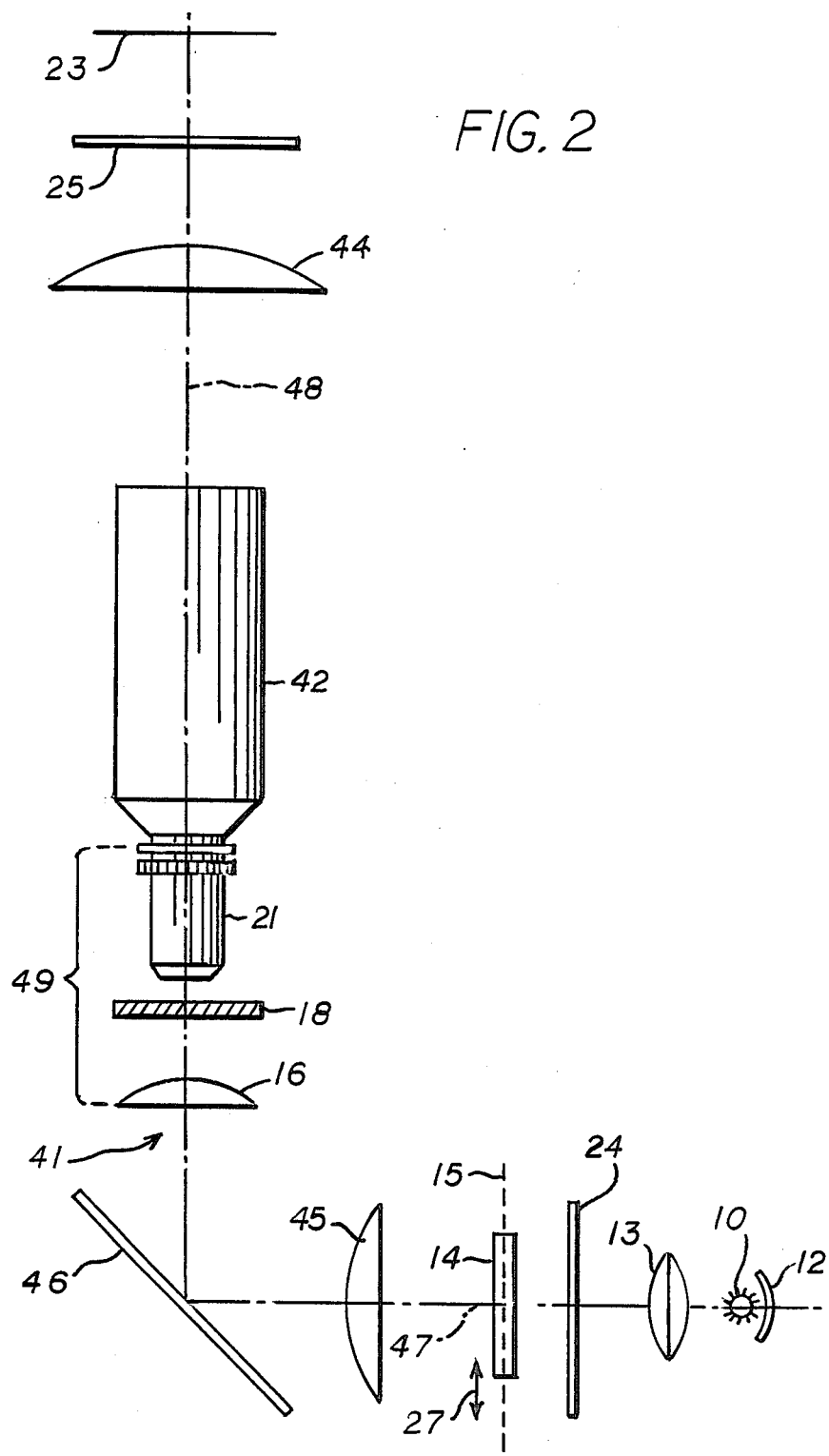
FIG. 2 is a similar view of an infinity corrected telescopic microscopy system according to another embodiment of the invention.

The scanning microscopy apparatus 41 shown in FIG. 2 employs infinity corrected optics with telescopic viewing, enabling optical sectioning with a minimum number of optical elements. Most of the components shown in FIG. 2 are the same as those in FIG. 1, and reference may be had to the above description of FIG. 1 with respect to such like or functionally equivalent components.

The microscope 42 also has an objective, like the microscope 20 shown in FIG. 1. However, in the embodiment of FIG. 2, a relay lens 44 replaces the traditional ocular for infinity corrected telescopic viewing. A corresponding relay lens 45 is provided for the condenser 16 in the input light path from the source 10.

The entire light path could be straight, such as shown at 38 in FIG. 1. However, light-deflecting means 46 re provided in the embodiment of FIG. 2. Suitable means for deflecting light from a path 47 into a path 48 include a front-surface mirror or a right-angle prism at 46.

The essential feature of the embodiment of the invention again is that the scanning aperture assembly 14 and thereby the array of light spots projected onto or into the object 18, is translatorily scanned, as indicated by the double-headed arrow 27.

Even though not shown in FIG. 2, that embodiment may also employ the camera, storage or recording and display system 31, 33 and 35, shown in FIG. 1 and herein disclosed in connection therewith.

With the infinity corrected telescopic viewing system of FIG. 2, change of the object plane of the system may be affected by merely moving the objective 21. As indicated at 49, the condenser 16 and objective 21 or microscope 42 may be coupled to be movable as a unit for viewing different depths in the object 18. In practice, the feasibility of such optical sectioning renders movement of the entire mass of the microscope system unnecessary, which can be important in microsurgery and other fields where movement of large masses would either be impractical or highly undesirable.

The embodiments of FIGS. 1 and 2, with or without one or both of the filters 24 and 25 and with or without the deflector 46, are primarily useful in transillumination microscopy. Examples of incident light microscopy within the scope of the subject invention will now be explained with the aid of FIG. 3.

Figure 3:
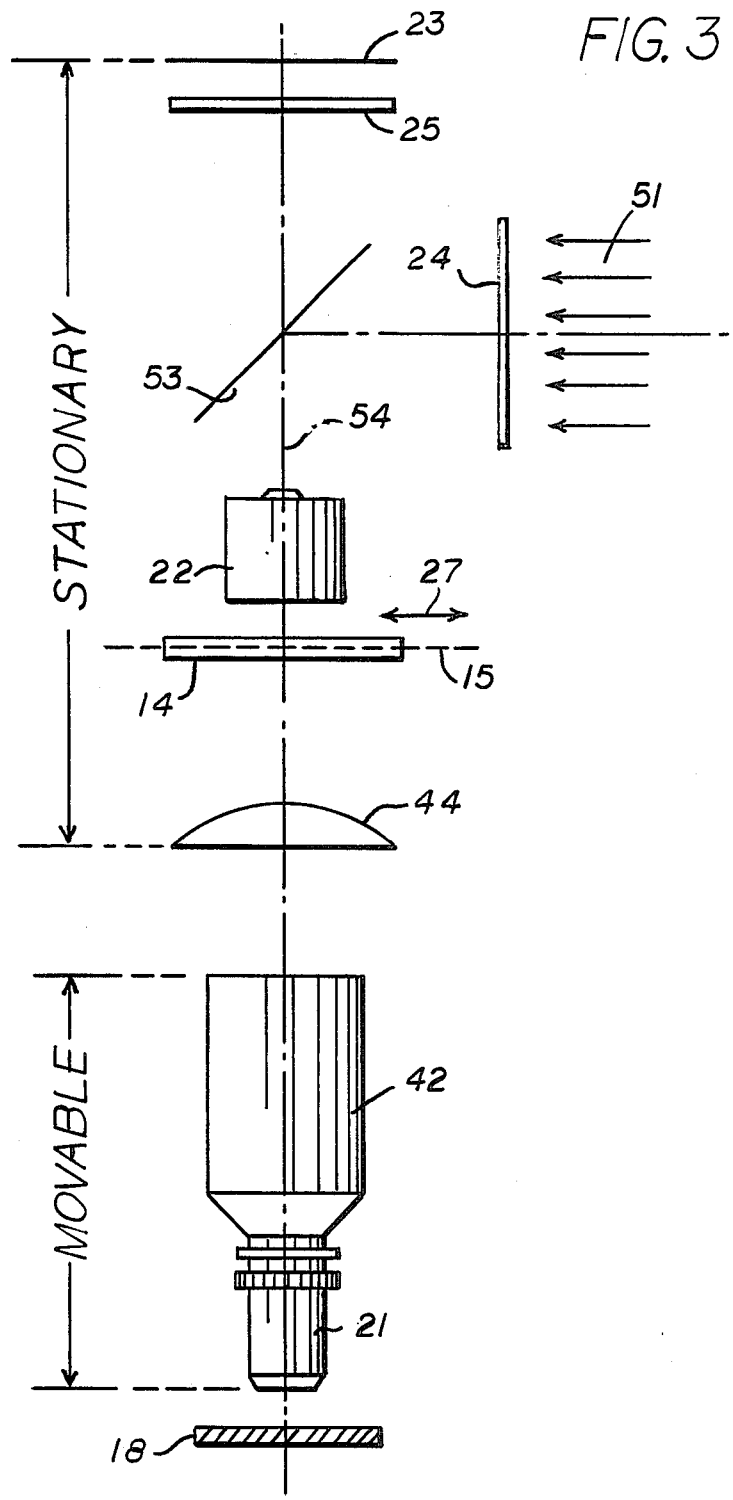
FIG. 3 is a similar view of a confocal incident light microscopy system according to a further embodiment of the invention.

By way of simplification, FIG. 3 merely shows illumination 51, rather than illustrating a light source with condenser lens, with or without reflector. However, the same components 10, 12 and 13 may be used in FIG. 3 as in FIGS. 1 and 2.

FIG. 3 also shows a relay lens 44 for infinity corrected telescopic viewing. For standard microscopic viewing, the relay lens 44 may be omitted. Telescopic viewing is, however, preferred where optical sectioning is necessary or desirable.

The preferably collimated illumination 51 is passed through the filter 24 to a beam splitter or dichroic mirror 53 which projects that light along the path 54 through the imaging ocular 22, scanning aperture assembly 14, relay lens 44, microscope 42 with objective 21, to the object 18. Due to the presence and operation of the scanning aperture assembly 14, such incident light is again in the form of a two-dimensional array of light spots scanning the object 18 translatorily. Reflections or other emanations resulting from such translatory scanning proceed along the path 54 through the objective 21 of microscope 42 and relay lens 44 to the imaging plane 15 of that relay lens. If that relay lens 44 is omitted for conventional microscopy, then the image plane 15 is the image plane of the objective 21. Similarly, 15 may be the image plane of the ocular 22 for incoming light 51.

In the embodiment of FIG. 3, the same apertures in the scanning assembly 14 are used for both the transmission of light 51 to the object and the transmission of light from that object 18, with the scanning assembly 14 being moved translatorily for both purposes, as indicated by the double-headed arrow 27 also in FIG. 3.

Light returning from the array of translatorily moving spots on the object 18 passes from the apertures in the scanning assembly 14 through the imaging ocular 22 and the beam splitter or dichroic mirror and second filter 25, to form again the observable or recordable optical image 23. As before, the human eye or a photographic or video camera may be used in the embodiment of FIG. 3, as illustrated at 31, 33 and 35 in FIG. 1, and as described above in connection therewith.

In the case of fluoroscopy, an excitation filter is again used at 24 and a barrier filter at 25. In practice, a dichroic mirror at 53 can perform at least part of the function of the barrier filter 25, in preventing illumination 51 used for exciting fluorescence in the object 18 from disturbing the optical image 23. This is particularly important where the same apertures are used for transmission of light in both directions, since there then is a danger of light reflection from the scanning assembly backwards through the light path 54. In that case, a dichoric mirror 53, with or without barrier filter 25 could eliminate such a reflection of primary light 51 into the optical image 23.

Even in the case of viewing with light reflected from the object 18, a polarizer 24 should be used in conjunction with an analyzer 25, since light reflections at the scanning assembly 14 can be eliminated from the optical image 23 in that manner.

A great practical advantage of the embodiment of FIG. 3 is that the components 22, 24, 25, 44 and 53 and their supporting structure may remain stationary, while only the microscope part 42 with objective 21 need to be movable for viewing the object 18 at different depths. Even the scanning assembly may be stationary, except for its translatory motion 27 and an initial or occasional adjustment.

Within the scope of the subject invention, the scanning assembly 14 could be a fiber optics bundle which proceeds from the light source 10 to the object 18 and which is translatorily moved transversely thereto, as indicated by the double-headed arrow 27 in the drawings. In such an arrangement, the array of fibers corresponds to the array of apertures presently to be described. The cross section of the fiber array at the object 18 could be square or rectangular, but such rectangularly arranged fibers could be bundled into a circular configuration at an end remote from the object 18. In that manner, light from a laser or other source emitting a circular beam could be better utilized, than if the fiber optics bundle were rectangular throughout its length. Apertures 62 may be fiber end surfaces.

FIG. 4 shows an example of a preferred embodiment of the invention providing a two-dimensional array 61 of apertures 62, transmitting light through these apertures, such as in the manner shown in FIGS. 1 to 3, to provide a two-dimensional array of light spots 63, such as shown in FIG. 5, on the object 18. That object is scanned with the two-dimensional array of light spots 63 by translatorily moving the two-dimensional array 61 of light-transmitting apertures 62 relative to the object, as indicated by the double-headed arrow 27, in the plane of that array, which may be the plane of the paper on which FIGS. 4 and 5 are drawn, while transmitting light through the apertures 62.

By way of example, the two-dimensional array 61 of light-transmitting apertures 62 is provided in a plate 65, and the scanning of the object 18 with the light spots 63 includes moving that plate translatorily in its plane as, for instance, indicated at 27. Where drilling and punching would provide too coarse an array, photographic, photolithographic or etching techniques may be employed for providing the aperture plate 65 with apertures 62 in the desired array 61.

The apertures themselves may, for instance, be square, rhomboid, round or circular as shown in FIGS. 4 and 5.

The aperture plate 65 may be movably mounted on a baseplate 67 by conventional flexure pivots 68 attached, for instance, to the four corners of the rectangular aperture plate. As indicated in part by a dotted outline 69, the baseplate 67 has an aperture for the transmission of light through the apertures 62 of the array 61.

In this respect, it has already been pointed out above in connection with FIG. 3 that the same apertures 62 in the plate 65 may be used for both the transmission of light to the object and a transmission of light of the spots 63 from that object 18. In the case of fluoroscopy, the latter light of the spots 63 is the light emanating from such spots in response to excitation causing fluorescence in the object. In the other case, the latter transmission of light from the object is the transmission of light reflected from the spots 63.

The baseplate 67 may be stationary, while the aperture plate 65 moves translatorily as shown at 27. Within the scope of the subject invention, this does not exclude an initial or occasional adjustment of the scanning aperture assembly. For instance, the baseplate may be mounted on a pivot which is shown at 71, but which may be located elsewhere, depending on the particular instrumentation and objective to be accomplished.

The baseplate 67 may be angularly moved about the pivot 71, for initial and occasional adjustment of the aperture array 61 relative to the object 18 or to components of the microscopic system. As shown at 72 in FIG. 4, a worm gear may be employed for that purpose. The baseplate 67 has a gear wheel section 73 attached thereto, and the worm 74 has a shaft 75 extending through a stationary bearing 76. A knob 78 on that shaft permits manual angular adjustment of the scanning aperture assembly.

However, it should be clearly understood that such angular motion, if any, is strictly for the purpose of initial and occasional adjustment, as distinguished from the scanning process itself. The subject invention only scans translatorily, such as indicated by the double-headed arrow 27. No angular scanning is contemplated by the subject invention, contrary to the case of the above mentioned prior-art Nipkow disc.

The translatory motion 27 may also be referred to as linear motion, if it is undertstood that such terminology does not exclude sinusoidal or other non-linear motion in the direction of the translatory motion. For instance, a drive 81 may impose a harmonic vibration or oscillation on the aperture plate 65. As indicated by the double-headed arrow 27, that would still be a translatory motion.

Within the scope of the subject invention, the drive 81 may be a mechanical drive with a suitable cam, a solenoid or other electromagnetic drive, or a piezo-electric drive.

In the latter cases, a signal generator 82 may be employed for electrically exciting the drive or actuator 81 into the desired translatory motion 27. In principle, a sawtooth form of excitation may be used, in which case the aperture plate 65 and thereby the light spots on the object 63 are subjected to a quick flyback between advance motions. Alternatively, a linear ramp function or a harmonic excitation may be employed, depending on the nature of the particular microscopy and the objective to be accomplished.

As shown at 83, the amplitude or frequency of the excitation and thereby of the translatory motion may be adjustable or variable.

In the preferred embodiment of FIG. 5, the two-dimensional array of light spots 63 is made rectangular, and the object 18 is scanned by translatorily moving that rectangular array of light spots over the object.

In viewing FIG. 5, it should be understood that optical means shown in FIGS. 1 to 3 image the apertures 62 onto the object 18 so that the light spots 63 are much smaller than the apertures 62.

According to that embodiment of the invention, the light spots 63 are arranged on intersections of parallel first lines 85 with parallel second lines 86 extending at an angle to the parallel first lines. Within the scope of the invention, the parallel lines 85 and 86 may extend at right angles to each other, or at less than right angles, whatever is best for the desired optimum coverage of the object 18 during scanning.

The object 18 is scanned by translatorily moving the light spots 63 at an angle 88 to the first and second lines 85 and 86, or to the lines 85 as shown in FIG. 5.

The apertures 62 in the scanning plate 65 may also be arranged in a rectangular array, as indicated at 61 in FIGS. 4 and 5. As there shown, the apertures 62 may be arranged or provided along or on intersections of parallel first lines 91 with parallel second lines 92, extending at an angle to the parallel first lines. As in the case of the parallel lines 85 and 86 for the light spots 63, the parallel lines 91 and 92 for the apertures 62 may extend at right angles to each other, or at any other angle that will provide optimum coverage of the scanned object 18.

As shown at 27 in FIG. 4, the aperture plate 65 is translatorily moved at an angle to the first and second parallel lines 91 and 92 on which the apertures 62 are arranged. The bottom of FIG. 5 shows by dotted outlines 94 an example of how coverage of the object 18 is increased by translatory motion of the aperture plate at an angle or angles to the parallel lines 91 and 92 of aperture location. In that example, about five steps of aperture travel or light spot travel are required to cover the object area between spots 63. Such required travel may be varied by adjusting the sweep angle, such as at 78.

The scanning aperture assembly of FIGS. 4 and 5 may be employed in any of the embodiments of FIGS. 1 to 3, or otherwise within the scope of the subject invention. The same applies to the scanning assembly 100 diagramatically shown in FIG. 6. The scanning aperture assembly of FIG. 4 or 6 may be employed at 14 in FIG. 1, 2 or 3, for instance.

In particular, the embodiment of the invention shown in FIG. 6 provides first parallel slits 101 in a first plate 102 and second parallel slits 103 in a second plate 104. The two-dimensional array of light transmitting apertures 63 is then provided by superimposing the first and second plates 102 and 104 so that the first and second parallel slits 101 and 103 intersect and extend at an angle to each other, such as a right angle. Typically, the first and second plates 102 and 104 will be closely adjacent to each other, even though FIG. 6 shows a somewhat exploded view for better comprehension o its contents.

The two-dimensional array of light spots 63 is then provided by transmitting light through the intersecting portions of the first and second parallel slits 101 and 103 to the object 18, such as in the manner shown in any of the FIGS. 1 to 3. It may be noted in this respect that the intersecting portions of the first and second parallel slits 101 and 103 pursuant to FIG. 6 in effect form light-transmitting apertures of the kind shown at 62 in FIGS. 4 and 5.

That resulting array of light-transmitting apertures is translatorily moved relative to the object 18 by sweeping the first plate 102 translatorily in the plane of that first plate at an angle to the first slits 101 and the second plate 104 translatorily in a plane of that second plate at an angle to the second slits 103, while transmitting light through intersections of the first and second slits 101 and 103 to scan the object 18 with the resulting two-793 dimensional array of light spots 63, generally as in FIG. 5.

According to an embodiment of the invention, one of the first and second plates is moved faster than the other of these first and second plates 102 and 104. According to the preferred embodiment illustrated in FIG. 6, one of the first and second plates, such as the plate 102, is moved stepwise and the other of these first and second plates, such as the plate 104, is moved more continuously. For instance, the second plate 104 may be moved translatorily as indicated by a double-headed arrow 127, identical or similar to the translatory motion indicated in other figures by the double-headed arrow 27. Accordingly, a drive or actuator 181 similar to the drive 81 may be employed for translatorily moving the plate 104. The signal generator 182 shown in FIG. 6 for driving the actuator 181 may also be the same as the signal generator 82 and its variations disclosed above.

On the other hand, the drive for the other plate 102 preferably includes a stepping motor 106 energized by a step-function signal generator 107 as indicated by dotted arrows 108 and 109 in FIG. 6.

One preferred mode of operation of the scanning assembly 100 is for the plate 104 to sweep in the direction of the slits 101, as indicated by arrow 127, while the stepping motor 106 maintains the other plate 102 stationary. After each sweep of the plate 104, the stepping motor 106 advances the slits 101 transversely thereto by one step, in the direction of arrow 108. In other words, the actuator 181 sweeps the slits 103 in the interval between each successive steps of the advance of the other plate 102.

As indicated by the dotted arrows 108 and 109, the stepping motor 106 may translatorily step the plate 102 both backward and forward.

However, within the scope of the invention, a fast flyback may be provided for the plate 102 at the end of each cycle of stepped advances, such as in the direction of the arrow 108. Similarly, a fast flyback may be provided for the plate 104 after each sweeping motion, such as in one of the directions of the double-headed arrow 127.

As already indicated above, the scanning aperture assembly 100 may be employed at 14 in the non-confocal embodiments of FIGS. 1 and 2 or in the confocal embodiment of FIG. 3 hereof. In the latter case, the same intersecting portions of the first and second parallel slits 101 and 103 may be used for both the transmission of light 51 to the object 18 and for the transmission of light from that object, such as upon reflection of lights from the spots 63 or upon excitation of fluorescence in the object in response to these scanning light spots. Light scattered and reflected by any of the plates of the scanner assembly 100 may be eliminated from the transmission of light from the object by an analyzer or barrier filter 25 and/or dichroic mirror 53, as already described above for the scanning assembly 14.

The baseplate 67 shown in FIG. 4 may be employed for mounting the scanning assembly 100 shown in FIG. 6. In that case, four flexure pivots 68 may be employed at the corners of the plate 104 for mounting the same on the baseplate 67. Similarly, four flexure pivots 68 may be employed at the four corners of the plate 102 for mounting the same on the baseplate 67 for motion independent of the different motion of the plate 104. The plates 102 and 104 may, however, be mounted by other kind of mounting means, inasmuch as each of the rectangular plates 102 and 104 need only be movable in parallel to one of its dimensions.

The means shown in FIG. 4 at 67 to 78 for varying the travel of translatory movement of the two-dimensional array of apertures 62 or light spots 63, as indicated at 94 in FIG. 5, may also be employed in the embodiment of FIG. 6, such as by mounting at least one of the plates 102 and 104 on the baseplate 67. In that case, these means also in FIG. 6 permit an adjustment of the sweep angle 88 of translatory movement for optimum coverage of the object 18 by translatorily moving light spots 63 as engendered by scanning intersections of slits 101 and 103. In such expansion of the embodiment of FIG. 6, as well as in the embodiment of FIGS. 4 and 5, the variation of the scanning angle, in turn, permits variation of the scanning amplitude, such as at 83.

In practice, one could adjust the translatory motion amplitude or travel, such as at 83, and the sweep angle 88, such as at 78, while observing the sweeping array of light spots 63, until optimum coverage of the object has been achieved for a given purpose by such translatory amplitude and sweep angle adjustments.

With the rapid expansion of very large scale integration (VLSI), the subject invention and its embodiments are becoming particularly useful in that area, including the inspection of VLSI circuitry, chips, masters and the like, where the extreme contrast and resolution provided by the subject invention are highly advantageous. In this and other areas, it is becoming increasingly interesting and even important to determine various responses of an object to illumination. In this respect, light reflection and fluorescence have already been mentioned above. Other responses within the scope of the invention include, for instance, electrical and other responses of photosensitive or photoelectric substances and materials to illumination.

Even though this invention manifests a radically different approach than the one disclosed in the above mentioned U.S. Pat. No. 3,517,980, issued Jun. 30, 1970, to M. Petran and M. Hadravsky, that patent, nevertheless, is herewith incorporated by reference herein for whatever of its teaching may be employed in the practice of the subject invention. This also applies to the useful teachings of the above mentioned papers of my colleagues, as well as to the teachings of my own papers, all of which are herewith incorporated by reference herein for that purpose.

The subject extensive disclosure will render apparent or suggest to those skilled in the art various modifications and variations within the spirit and scope of the subject invention and equivalents thereof.

I claim:

1. In a method of improving contrast and resolution of a predetermined response of an object to illumination, the improvement comprising in combination the steps of:

providing a two-dimensional array of light-transmitting apertures in a plate;

transmitting light through said apertures to provide a two-dimensional array of light spots on the object; and using the same apertures in said plate for both said transmitting of light to the object and a transmission of light of said spots from the object.

2. In apparatus for improving contrast and resolution of a predetermined response of an object to illumination, the improvement comprising in combination:

a plate having a two-dimensional array of light-transmitting apertures therethrough;

means for transmitting light through said apertures to provide a two-dimensional array of light spots on the object;

means for scanning the object with said two-dimensional array of light spots, including means for moving said plate linearly in its plane relative to the object while said means for transmitting light transmit light through said apertures; and a microscopy system having means for using the same apertures in said plate for both said transmitting of light to the object and a transmission of light of said spots from the object.

3. In a method of improving contrast and resolution of a predetermined response of an object to illumination, the improvement comprising in combination the steps of:

arranging said light spots on intersections of parallel first lines with parallel second lines extending at an angle to said parallel first lines;

making a two-dimensional array of light spots translatorily movable in a plane of the array; and scanning the object by translatorily moving said two-dimensional array of light spots over the object at an angle to said first and second lines.

4. A method as claimed in claim 1, including the step of:

viewing sequential signals of light from the object scanned with said translatorily moving two-dimensional array of light spots.

5. A method as claimed in claim 1, including the step of:

recording sequential responses of the object to said translatorily moving two-dimensional array of light spots.

6. A method as claimed in claim 1, including the steps of:

storing sequential responses of the object to said translatorily moving two-dimensional array of light spots; and subsequently reproducing said stored sequential responses for observation.

7. A method as claimed in claim 1, including the steps of:

making said two-dimensional array of light spots rectangular; and scanning the object by translatorily moving said rectangular array of light spots over the object.

8. In a method of improving contrast and resolution of a predetermined response of an object to illumination, the improvement comprising in combination the steps of:

making a two-dimensional array of light spots translatorily movable in a plane of the array;

scanning the object by translatorily moving said two-dimensional array of light spots over the object; and varying a travel of translatory movement of said two-dimensional array of light spots, as required for coverage of said object, by adjustment of a sweep angle of said translatory movement.

9. In a method of improving contrast and resolution of a predetermined response of an object to illumination, the improvement comprising in combination the steps of:

providing a two-dimensional array of light-transmitting apertures;

transmitting light through said apertures to provide a two-dimensional array of light spots on the object; and scanning the object with said two-dimensional array of light spots by translatorily moving said two-dimensional array of light-transmitting apertures relative to the object in the plane of that array while transmitting light through said apertures said two-dimensional array of light spots being adjustable by angular motion.

10. A method as claimed in claim 9, wherein:

said two-dimensional array of light-transmitting apertures is provided in a plate; and said scanning of the object includes moving said plate translatorily in its plane.

11. A method as claimed in claim 10, including the step of:

using the same apertures in said plate for both said transmitting of light to the object and a transmission of light of said spots from the object.

12. A method as claimed in claim 9, including the step of:

eliminating from said transmission of light from the object light scattered and reflected by said plate.

13. In a method of improving contrast and resolution of a predetermined response of an object to illumination, the improvement comprising in combination the steps of:

providing first parallel slits in a first plate;

providing second parallel slits in a second plate;

providing a two-dimensional array of light-transmitting apertures by superimposing said first and second plates so that said first and second parallel slits intersect and extend at an angle to each other;

providing a two-dimensional array of light spots on the object by transmitting light through intersecting portions of said first and second parallel slits to the object; and translatorily moving said two-dimensional array of light-transmitting apertures by sweeping said first plate translatorily in the plane of said first plate at an angle to said first slits and said second plate translatorily in a plane of said second plate at an angle to said second slits, while transmitting light through intersections of said first and second slits to scan the object with the resulting two-dimensional array of light spots.

14. A method as claimed in claim 13, wherein:

one of said first and second plates is moved faster than the other of said first and second plates.

15. A method as claimed in claim 13, wherein:

one of said first and second plates is moved stepwise and the other of said first and second plates is moved more continuously.

16. A method as claimed in claim 13, including the step of:

using the same intersecting portions of said first and second parallel slits for both said transmitting of light to the object and a transmission of light of said spots from the object.

17. A method as claimed in claim 16, including the step of:

eliminating from said transmission of light from the object light scattered and reflected by any of said plates.

18. In a method of improving contrast and resolution of a predetermined response of an object to illumination, the improvement comprising in combination the steps of:

providing a two-dimensional array of light-transmitting apertures;

transmitting light through said apertures to provide a two-dimensional array of light spots on the object;

scanning the object with said two-dimensional array of light spots by translatorily moving said two-dimensional array of light-transmitting apertures relative to the object in the plane of that array while transmitting light through said apertures; and varying a travel of translatory movement of said two-dimensional array of light-transmitting apertures, as required for coverage of said object, by adjustment of a sweep angle of said translatory movement.

19. In apparatus for improving contrast and resolution of a predetermined response of an object to illumination, the improvement comprising in combination:
- means for providing a two-dimensional array of light spots situated on intersections of parallel first lines with parallel second lines extending at an angle to said parallel first lines;
- means for rendering said two-dimensional array of light spots translatorily movable in a plane of the array; and
- means for scanning the object, including means for translatorily moving said two-dimensional array of light spots over the object at an angle to said first and second lines.

20. Apparatus as claimed in claim 19, including:
- means for rendering sequential signals of light from the object scanned with said translatorily moving two-dimensional array of light spots viewable.

21. Apparatus as claimed in claim 19, including:
- means for recording sequential responses of the object to said translatorily moving two-dimensional array of light spots.

22. Apparatus as claimed in claim 19, including:
- means for storing sequential responses of the object to said translatorily moving two-dimensional array of light spots; and
- means connected to said storing means for subsequently reproducing said stored sequential responses for observation.

23. Apparatus as claimed in claim 19, wherein:
- said two-dimensional array of light spots is rectangular; and
- said means for scanning the object include means for translatorily moving said rectangular array of light spots over the object.

24. In apparatus for improving contrast and resolution of a predetermined response of an object to illumination, the improvement comprising in combination:
- means for providing a two-dimensional array of light spots;
- means for rendering said two-dimensional array of light spots translatorily movable in a plane of the array;
- means for scanning the object, including means for translatorily moving said two-dimensional array of light spots over the object; and
- means for initially and occasionally adjusting said means for providing a two-dimensional array of light spots, including means for angularly moving the latter means.

25. In apparatus for improving contrast and resolution of a predetermined response of an object to illumination, the improvement comprising in combination:
- means for providing a two-dimensional array of light spots;
- means for rendering said two-dimensional array of light spots translatorily movable in a plane of the array;
- means for scanning the object, including means for translatorily moving said two-dimensional array of light spots over the object; and
- means for varying a travel of translatory movement of said two-dimensional array of light spots as required for coverage of said object, including means for adjusting a sweep angle of said translatory movement.

26. In apparatus for improving contrast and resolution of a predetermined response of an object to illumination, the improvement comprising in combination:
- means for providing a two-dimensional array of light-transmitting apertures;
- means for transmitting light through said apertures to provide a two-dimensional array of light spots on the object;
- means for scanning the object with said two-dimensional array of light spots, including means for translatorily moving said two-dimensional array of light-transmitting apertures relative to the object in the plane of said array while said means for transmitting light transmit light through said apertures; and
- means for varying a travel of translatory movement of said two-dimensional array of light-transmitting apertures as required for coverage of said object, including means for adjusting a sweep angle of said translatory movement.

27. Apparatus as claimed in claim 26, wherein:
- said means for providing the two-dimensional array of light-transmitting apertures include a plate having said apertures therethrough; and
- said means for translatorily moving said two-dimensional array include means for moving said plate linearly in its plane.

28. Apparatus as claimed in claim 27, including:
- a microscopy system having means for using the same apertures in said plate for both said transmitting of light to the object and a transmission of light of said spots from the object.

29. Apparatus as claimed in claim 28, including:
- means for eliminating from said transmission of light from the object light scattered and reflected by said plate.

30. In apparatus for improving contrast and resolution of a predetermined response of an object to illumination, the improvement comprising in combination:
- a first plate having first parallel slits;
- a second plate having second parallel slits and being superimposed on said first plate so that said first and second parallel slits intersect and extend at an angle to each other;
- means for providing on said object a two-dimensional array of light spots, including means for transmitting light through intersecting portions of said first and second parallel slits to the object; and
- means for translatorily moving said two-dimensional array of light spots, including means for sweeping said first plate translatorily in the plane of said first plate at an angle to said first slits and said second plate translatorily in a plane of said second plate at an angle to said second slits, while said light transmitting means transmit light through intersections of said first and second slits to scan the object with the resulting two-dimensional array of light spots.

31. Apparatus as claimed in claim 30, wherein:
- said sweeping means include means for moving one of said first and second plates faster than the other of said first and second plates.

32. Apparatus as claimed in claim 31, including:
- means for varying a travel of translatory movement of said two-dimensional array of light-transmitting apertures as required for coverage of said object, including means for adjusting a sweep angle of said translatory movement.

33. Apparatus as claimed in claim 30, wherein:

said sweeping means include means for moving one of said first and second plates stepwise, and means for moving the other of said first and second plates more continuously.

34. Apparatus as claimed in claim 30, including:
a microscopy system having means for using the same intersecting portions of said first and second parallel slits for both said transmitting of light to the object and a transmission of light of said spots from the object.

35. Apparatus as claimed in claim 34, including:
means for eliminating from said transmission of light from the object light scattered and reflected by any of said plates.

* * * * *